United States Patent
Juhl et al.

(10) Patent No.: US 9,513,014 B2
(45) Date of Patent: *Dec. 6, 2016

(54) MEDICAL DEVICE FOR PREPARING THERMOPLASTIC MATERIAL

(71) Applicant: S&S X-Ray Products, Inc., Houston, TX (US)

(72) Inventors: Torben Juhl, Arslev (DK); Katarina Hansen, Kerteminde (DK); Torben Rasmussen, Odense S (DK); Norman Shoenfeld, Cypress, TX (US); Fred Sopenoff, Magnolia, TX (US)

(73) Assignee: S&S X-Ray Products, Inc., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/595,538

(22) Filed: Jan. 13, 2015

(65) Prior Publication Data

US 2015/0122795 A1    May 7, 2015

Related U.S. Application Data

(63) Continuation of application No. 14/048,181, filed on Oct. 8, 2013, now Pat. No. 8,957,350.

(51) Int. Cl.
| | |
|---|---|
| *F27D 11/00* | (2006.01) |
| *F24C 7/08* | (2006.01) |
| *A61M 5/44* | (2006.01) |
| *F24C 15/16* | (2006.01) |
| *F24C 15/32* | (2006.01) |
| *A61F 13/04* | (2006.01) |

(52) U.S. Cl.
CPC ............... *F24C 7/087* (2013.01); *A61M 5/44* (2013.01); *F24C 15/16* (2013.01); *F24C 15/325* (2013.01); *A61F 13/04* (2013.01)

(58) Field of Classification Search
CPC ........ H05B 3/68; F24C 15/322; F24C 15/325; F24C 7/06; F24C 7/087; F24C 15/006
USPC ....... 219/200, 201, 209, 211, 212, 217, 218, 219/385, 386, 387, 391, 400, 405, 407, 219/412, 417, 443.1, 449.1; 432/33; 604/114, 291

See application file for complete search history.

(56) References Cited

U.S. PATENT DOCUMENTS

| | | | |
|---|---|---|---|
| 5,466,912 A | 11/1995 | Dornbush et al. | 219/400 |
| 5,601,070 A | 2/1997 | Hotard et al. | 126/21 A |
| 5,816,797 A | 10/1998 | Shoenfeld | 432/33 |
| 7,138,613 B1 | 11/2006 | Walsh et al. | 219/521 |
| 8,138,452 B2 | 3/2012 | Thomas et al. | 219/400 |
| 8,258,435 B2 | 9/2012 | Bonuso et al. | 219/400 |
| 8,304,695 B2 | 11/2012 | Bonuso et al. | 219/400 |
| 2002/0121555 A1* | 9/2002 | Cipolla | G06F 9/52 236/49.1 |
| 2004/0040950 A1* | 3/2004 | Carbone | F24C 15/325 219/400 |
| 2005/0211696 A1 | 9/2005 | Adamski | 219/400 |

(Continued)

*Primary Examiner* — Dana Ross
*Assistant Examiner* — James Sims, III
(74) *Attorney, Agent, or Firm* — Sunstein Kann Murphy & Timbers LLP

(57) ABSTRACT

A device for preparing a thermoplastic material, with dry heat, for use in patient fixation. The device generates circulated heat to a threshold temperature. Once the thermoplastic material has become pliable, it is molded into a cast for fixation purposes. The circulated heat may be generated by a device having a housing and a support member movably attached to the housing. The device also includes a heating element and an array of circulation elements.

16 Claims, 7 Drawing Sheets

(56) References Cited

U.S. PATENT DOCUMENTS

| | | | |
|---|---|---|---|
| 2007/0107712 A1 | 5/2007 | Shiraichi et al. | 126/21 A |
| 2007/0211430 A1 | 9/2007 | Bechtolsheim | 361/695 |
| 2008/0210102 A1 | 9/2008 | Rabas | 99/447 |
| 2010/0147825 A1 | 6/2010 | Bonuso et al. | 219/400 |
| 2011/0044799 A1 | 2/2011 | Takemoto et al. | 415/143 |
| 2012/0274252 A1 | 11/2012 | He | 318/430 |
| 2012/0287571 A1 | 11/2012 | Santos | 361/679.48 |
| 2013/0167828 A1* | 7/2013 | Trice | F24C 15/16 126/339 |
| 2013/0291854 A1* | 11/2013 | Johnson | F24C 15/16 126/21 A |

* cited by examiner

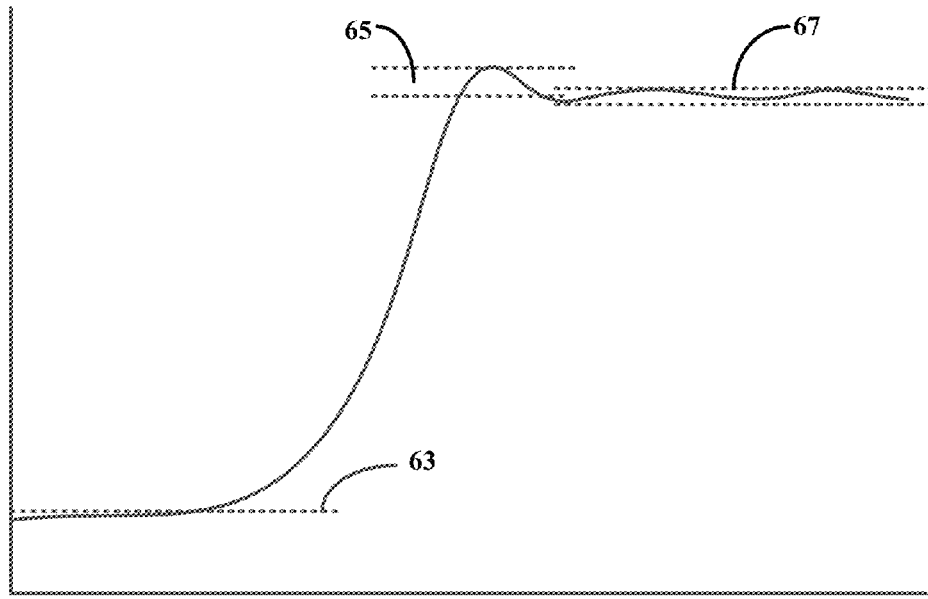
*Fig. 9*
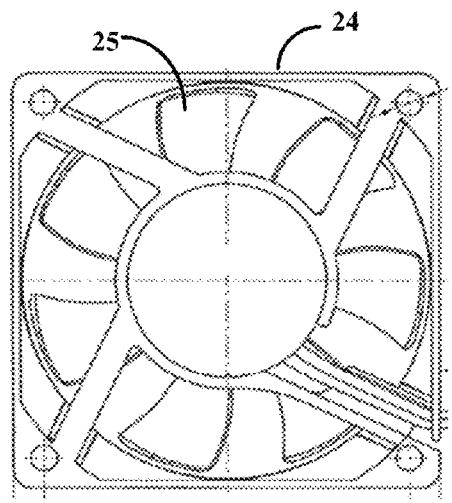   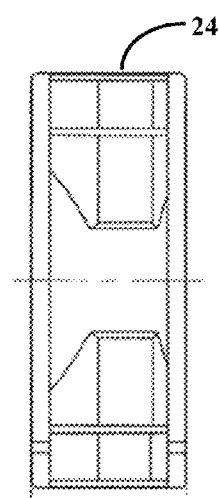
*Fig.10(a)*    *Fig.10(b)*

MEDICAL DEVICE FOR PREPARING THERMOPLASTIC MATERIAL

The present application is a continuation application of U.S. application Ser. No. 14/048,181, filed Oct. 8, 2013, the full disclosure of which is hereby incorporated by reference herein.

TECHNICAL FIELD

The present invention generally relates to a medical device for preparing thermoplastic materials, and in particular, to a medical device for warming thermoplastic materials for use in patient fixation.

BACKGROUND ART

When carrying out certain medical procedures, for example, radiation therapy or orthopedic settings, thermoplastic materials are frequently used on a patient for fixation (i.e., casting) purposes. In general, thermoplastic materials, when warmed to a temperature within a threshold range, become easily pliable, and, when cooled below that threshold range, become relatively rigid. To this end, thermoplastic materials are often warmed and molded into a shape which complements a body part on a patient, so as to help the patient maintain that particular body part in a required fixed position for an extended period of time or to replicate that exact position over the course of multiple treatments. For example, in radiation therapy involving the head area, a patient may find it difficult to maintain his or her head in a certain position for the entire treatment or to replicate the same fixed position between treatments. As such, a thermoplastic material may be warmed and molded into a cast corresponding to the shape of the patient's head for maintaining the patient's head in the required position. The thermoplastic material may also be used for orthopedic purposes. For example, by setting a cast of thermoplastic material about an arm or leg having a bone fracture, movement of the arm or leg may be minimized to aid in the healing of the fracture.

Currently, to transform the thermoplastic material from a relatively rigid to a more pliable state, the thermoplastic material is heated in a warming chamber by a conductive heat-source. An example of such a warming chamber is disclosed in U.S. Pat. No. 5,816,797.

The thermoplastic material may alternatively be soaked in a hot water bath to provide uniform heating. However, a water bath is generally bulky and large in size and, therefore, may take up much of the needed space in a limited work area. Moreover, the bath may need to be both refilled and cleaned regularly due to issues associated with evaporation and bacterial growth. The cleaning presents spillage hazard for people and instruments in the vicinity of the water bath.

Accordingly, it is desirable that a cast for fixation purposes be formed from a thermoplastic material that has been warmed to a pliable state more quickly and reliably than existing warming chambers.

SUMMARY OF THE EMBODIMENTS

In accordance with one embodiment of the present invention, a countertop or portable apparatus is provided for warming a thermoplastic material, for instance, polycaprolactone, for use on a patient. The apparatus provides circulated dry heat to uniformly heat the volume of the thermoplastic material so that the material may be used for fixation purposes. The circulated dry heat transforms the thermoplastic material from a relatively rigid state to a more pliable state. The apparatus includes a housing defining a warming chamber having a central region and a periphery region. A support member is disposed in the warming chamber for supporting a thermoplastic material. The support member may have a non-stick surface. A heating element is disposed in the warming chamber for distributing heat uniformly over a planar surface area coincident with the support member. An array of circulation elements, disposed in the warming chamber, is capable of circulating air within the chamber. The circulation elements are preferably disposed so as to move air both above and below the support member. In an embodiment, the array of circulation elements is disposed above and below the support member.

In an embodiment, the array of circulation elements includes at least three fans. The fans are preferably disposed in horizontal alignment. In one arrangement of the fans, at least one fan pushes air centrally at the central region and at least two fans draw air from the periphery region, concurrently. In another preferred embodiment, the array of circulation elements includes at least four fans with at least two elements pushing air centrally and at least one element drawing air from each periphery region concurrently. A thermal sensor may be placed between a first and second element of the array. Each of the circulation elements is capable of generating flow of at least 30 cubic feet per minute (CFM), preferably between about 40 and 60 CFM, even more preferably between about 45 and 55 CFM. The device preferably includes an insulating member to maintain heat within the warming chamber and to attenuate noise generated by the circulation elements, as well as the movement of air in the chamber. A voltage waveform circuit may be employed to reduce the noise generated by the circulation elements.

In an embodiment, the heating element is (i) configured as a planar surface spanning the central and periphery regions of the warming chamber and (ii) disposed below the support member. The heating element is capable of generating heat within a threshold range necessary for transforming the thermoplastic material into a more pliable state. The heating element may generate the heat in a manner that the temperature over its entire surface is uniform.

In an embodiment, the housing includes a panel to form a drawer that alternatively moves between a closed position and an open position with respect to the warming chamber. The housing may be connected to the support member. The heating element and the array of circulation elements may be configured to operate only when the drawer is in the closed position. The housing may include a mounting member for the support member to seat. To this end, the support member may be disconnected from the support member for cleaning. In an embodiment, the mounting member may include a quick disconnect mechanism for securing the support member to the mounting member.

A thermal regulator ramps and maintains the temperature within the warming chamber in a precise manner. The ramp preferably does not exceed two degrees Fahrenheit of a set temperature. The thermal regulator maintains the warming chamber at the set temperature. The regulation results in a variation of the temperature in the warming chamber preferably less than one degree Fahrenheit from the set temperature.

In accordance with one embodiment of the present invention, the apparatus includes a controller having a memory for storing information associated with different thermoplastic materials to be used for fixation purposes. The information includes operating temperature information. To this end, a user can select a thermoplastic material from a list displayed at a graphical user interface of the controller. The selection being sufficient to set the desired warming temperature specific for the selected thermoplastic material. The warming temperature may be a maximum rated temperature value for a given thermoplastic material. Other operating temperatures may be stored, including a drop-down temperature value for the thermoplastic material. The controller may display an image of the thermoplastic material on the graphical user interface, as well as information associated with the fixation of the thermoplastic material.

BRIEF DESCRIPTION OF THE DRAWINGS

The foregoing features of embodiments will be more readily understood by reference to the following detailed description, taken with reference to the accompanying drawings, in which:

FIG. 9 is a diagram showing the temperature regulation of the device.

FIGS. 10(a) and 10(b) are diagrams of circulation elements within the device of FIG. 1.

DETAILED DESCRIPTION OF SPECIFIC EMBODIMENTS

Figure 1:
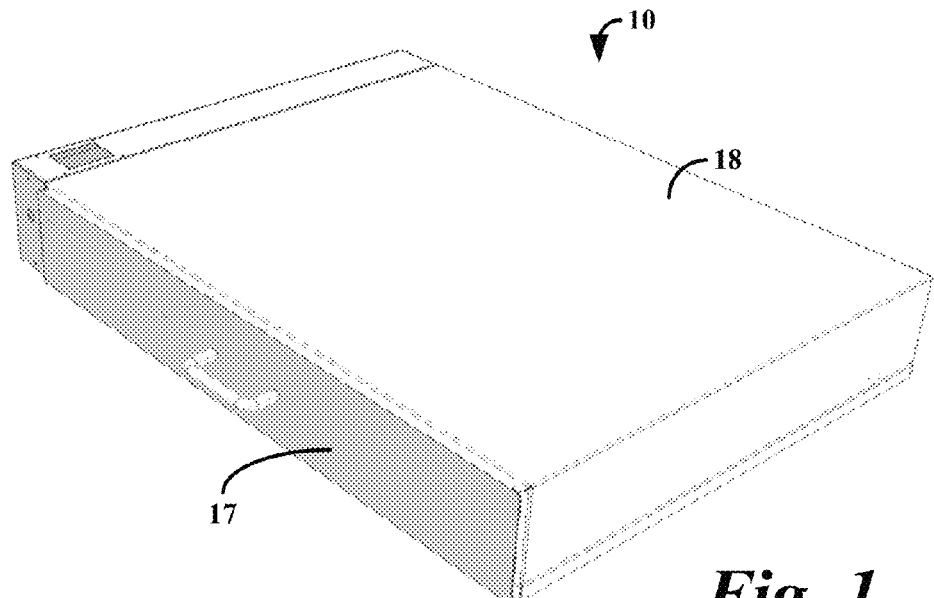
FIG. 1 is a perspective view of a warming chamber portion of an apparatus for warming thermoplastic materials for purposes of patient fixation.
Figure 2:
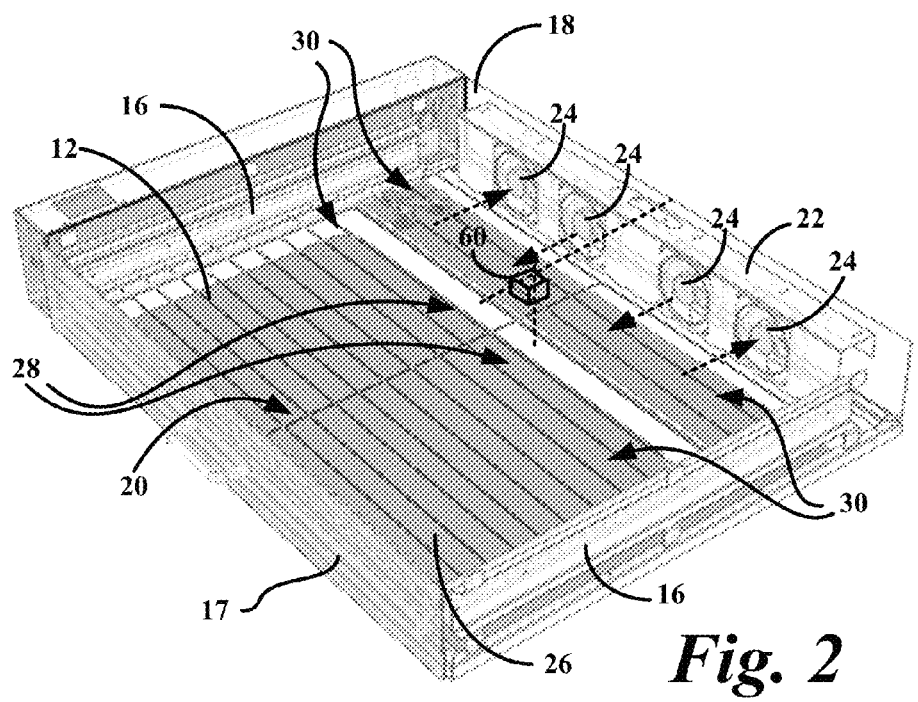
FIG. 2 is a perspective view of the device of FIG. 1.
Figure 5:
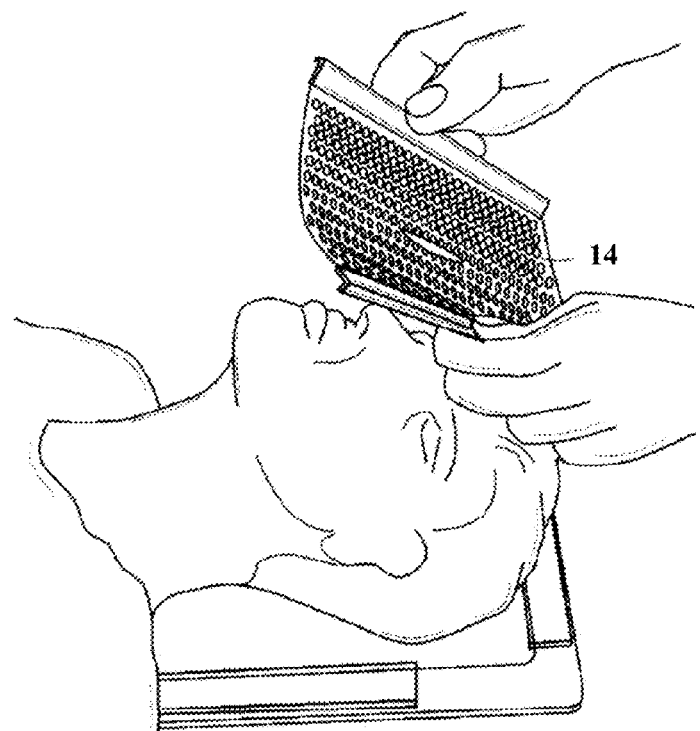
FIGS. 5 and 6 illustrate a thermoplastic material being used for fixation purposes.
Figure 6:
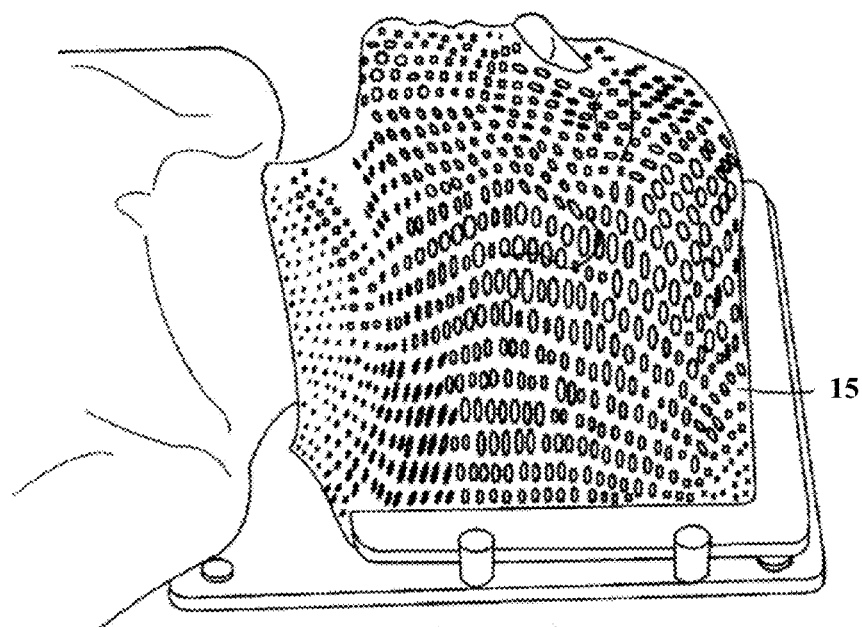

Referring now to the drawings, FIGS. 1 and 2 illustrate a device 10 for dry warming a thermoplastic material 14 from which a cast may be formed in accordance with the present invention. The device 10 includes a support member 12 for a thermoplastic material 14 to form the cast 15 (see FIGS. 5 and 6). The support member 12 is attached to a mounting member 16 located within a housing 18 defining a warming chamber 20. An array 22 of circulation elements 24 is disposed in the warming chamber 20 to cause a movement of heated air in the warming chamber 20. The air is heated by a heating element 26 disposed in the warming chamber 20. In one embodiment of the invention, the array 22 of circulation elements 24 includes at least three horizontally aligned circulation elements 24.

During operation, the array 22 of circulation elements 24 moves air about throughout the warming chamber 20. The circulation elements 24 are arranged to promote uniform heating over the entirety of the top and bottom surfaces of a thermoplastic material 14 lying on the support member 12. It has been found that uniformity is enhanced when the circulation elements 24 push air centrally at a central region 28 of the warming chamber 20 while concurrently drawing air from the periphery regions 30 of the chamber 20. Nevertheless, other arrangements of the circulation elements 24 may also be used within the scope of embodiments of the present invention. Each circulation element 24 generates a flow, preferably, of at least 30 cubic feet per minute (CFM), preferably between about 40 and 60 CFM, even more preferably between about 45 and 55 CFM. The resulting movement of heated air in the warming chamber 20 improves the transfer of heat to the thermoplastic material 14 and prevents the formation of localized heated air pockets in the warming chamber 20. To this end, the temperature along different locations of the thermoplastic material 14 can reach a steady state with the temperature of the warming chamber 20 more quickly and with less variability than with passive convective heating only. In the preferred embodiment, the time may be less than five minutes, and the variation in the temperature may be less than one degree Fahrenheit.

Still referring to FIGS. 1 and 2, the warming chamber 20, in a preferred embodiment of the invention, is designed to hold a sheet 34 of thermoplastic material 14 measuring up to approximately 18 inches long, 24 inches wide, and about 0.25 inch thick. To this end, the array 22 of circulation elements 24 is designed to be integrated in a housing 18 that measures only slightly larger than that of the thermoplastic material 14. In this manner, the device 10 may be stored neatly, as a countertop or portable device, without taking up needed space in a work area. In an embodiment of the invention, the array 22 of circulation elements 24 comprises tubular fans, each measuring about 2.75 inches wide, about 1 inch deep, and about 2.75 inches high, and the housing 18 measures approximately 31.125 inches wide, 23 inches deep, and 4.7 inches high. In the preferred embodiment, the circulation elements 24 are DC brushless fans. It should be appreciated that other types of circulation elements may be employed, including, for example, permanent magnet fans, centrifugal fans, impeller fans, and blowers. The circulation elements 24 are preferably designed as a single horizontally-aligned array disposed at the rear of the warming chamber 20 to provide high movements of the heated air within the warming chamber 20 while maintaining the low and wide profile of the housing 18. The orientation of the circulation elements 24 in the array 22 promotes a generally uniform distribution of heat within the entirety of the warming chamber 20 or at least at that portion containing the thermoplastic material 14. The elements 24 are preferably aligned to the same plane coincident with the array 22, though they may be aligned at different angles in other embodiments. Identical circulation elements 24 may be, and are preferably, employed in the array 22. Of course, non-identical circulation elements 24, for example having different blade pitch or flow output, can be employed.

FIGS. 10(a) and 10(b) show a preferred embodiment of the circulation element 24. The circulation element is capable of pushing air from, as well as drawing air into, the blade 25 along a direction parallel to its axis of rotation. To this end, the circulation elements 24 in the array 22 preferably move heated air directly above and below the support member 12 and thus a sheet 34 of thermoplastic material 14 placed thereon. In this manner, a uniform convective heating and phase transformation of the thermoplastic material 14 is provided. As the housing 18 and support member 12 must withstand temperatures within a range sufficient to transform the thermoplastic material 14 from a relatively rigid state to a more pliable state, the housing 18 and support member 12 are preferably made from a strong metallic material such as stainless steel. Of course, the housing 18 and the support member 12 may be made from other metallic or non-metallic materials. Similarly, the array 22 of circulation elements 24 must also withstand temperatures within a range sufficient to transform the thermoplastic material 14 from a relatively rigid state to a more pliable state. The circulation elements 24 are preferably made from thermoplastic materials that are heat-resistant above 200° F., more preferably above 350° F., including polybutylene terephthalate (PBT). Of course, metallic material may alternatively be employed.

Figure 11A:
FIGS. 11(a) and 11(b) are diagrams of a heating element within the device of FIG. 1.
Figure 11B:
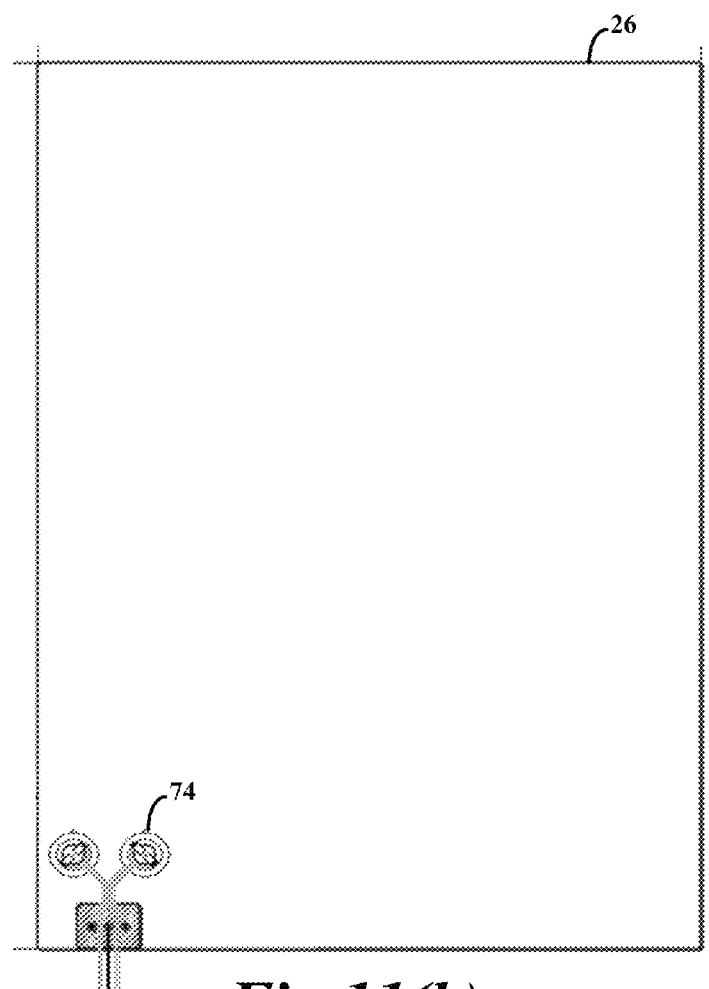

Looking now at FIGS. 3 and 4, the array 22 of circulation elements 24 straddles above and below the support member 12 to promote circulation of heated air along both sides of the support member 12 and the thermoplastic material 14 to be placed thereon. The support member 12 is preferably disposed below the central axis of the array 22 of circulation elements 24. The configuration promotes more circulation of the heated air in the top space above the support member 12 than the bottom space below the support member 12 to provide uniform heat distribution in the warming chamber 20 even though the heating element 26 is in proximity to the bottom region of the thermoplastic material 14. The circulation accelerates the transformation of the thermoplastic material 14 from a relatively rigid state to a more pliable state. The heating element 26 provides the heated air to convect to the support member 12 and preferably heats uniformly over its entire surface. The support member 12 preferably spans the central 28 and periphery regions 30 of the warming chamber 20. The heating element 26 can preferably generate heat to within a threshold range of from about 140° F. (degrees Fahrenheit) to about 180° F., necessary for transforming the thermoplastic material from a relatively rigid state to a more pliable state. The heating element 26 is preferably sized with a shape similar in dimensions to that of the support member 12 and at least larger than the sheet 34 of thermoplastic materials 14. To that end, the heat generated by the heating element 26 may be uniformly distributed across the entirety of the support member 12. The heating element 26 is capable of generating heat preferably at least 1 Watt per square inch (W per in$^2$), more preferably between 1.5 W per in$^2$ and 4 W per in$^2$. In the preferred embodiment of the invention, the heating element 26 may be a silicone-based heating element, similar to a flexible 1300 Watt 120/240V silicone-based etched foil sheet, such as that shown in FIGS. 11(a) and 11(b). In the embodiment, the sheet has a power density of about 2.64 Watt per inch$^2$ over a heat area of about 490 square inches and measures about 27.5 inches wide, about 18.5 inches deep, and about 0.2 inch thick. The temperature of the heating element 26, when energized, is preferably uniform over its entire surface. As shown in the FIG. 11(a), an etch foil 78 is encapsulated between two thermally insulating layers 80, made preferably of silicone rubber and fiberglass fabric composite. Of course, other types, sizes, operating voltages, and power densities may be employed. In combination with the array 22 of circulation elements 24, the heating element 26 is capable of heating a typical thermoplastic material 14, such as polycaprolactone, and transforming it to a pliable state in less than five minutes. Of course, depending on the thickness dimension and composition of the thermoplastic material 14, this preparation time may vary between about five and fifteen minutes. Although a silicone-based heating element are presently preferred, it should be appreciated that other heating elements, such as a conventional copper-wire mesh heating element, may be used so long as heat is generated substantially uniformly across the support member 12.

Referring back to FIGS. 3 and 4, the support member 12 is attached to a mounting member 16, which is capable of alternatively moving between an open position, as shown in FIG. 4, and a closed position, as shown in FIG. 1, with respect to the housing 18.

The mounting member may have a lip for the support member 12 to seat. To that end, the support member 12 is alternatively connectable and removable from the mounting member 16 for cleaning. The support member 12 may be composed of several member sections. The mounting member 16 may include a quick disconnect mechanism for securing the support member 12 to the mounting member 16. A front panel 17 forms the front face of the housing 18. The front panel 17 may be fixably mounted to the support member 12 so that the warming chamber 20 is formed when the support member 12 is pushed into the closed position. A sensor 64 (see FIG. 7) monitors the position of the support member 12, the mounting member 16, or the front panel 17 to disengage the array 22 of circulation elements 24 when it is not in a fully closed position. In this manner, the circulation of heated air in the warming chamber 20 ceases, and heat is thereby substantially maintained in the warming chamber 20 when the warming chamber 20 is not fully closed.

It has been found that the described configuration allows the warming chamber 20 to reach its set temperature quickly. In an embodiment, the time to transform a sheet 34 of the thermoplastic material 14 from a rigid state to a pliable state is less than five minutes. To this end, the heating element 26 is fixed to the housing 18 within the warming chamber 20, preferably below the support member 12 and spans the central 28 and periphery regions 30 of the warming chamber 20. The housing 18, thus, shields the heating element 26 from external air currents outside the warming chamber 20 so as to retain its heat. Of course, in other embodiments, the heating element 26 may be mounted either directly against the support member 12 or within the mounting member 16 so that it sits directly against and beneath the support member 12.

Figure 3:
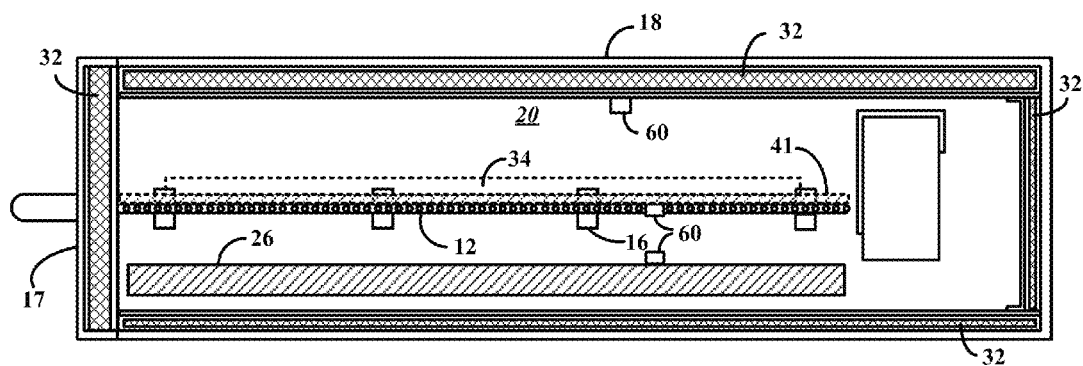
FIG. 3 is a cross-sectional view of the device shown in FIGS. 1 and 2.

Insulating members 32, still looking at FIG. 3, are preferably installed within the top, side, front, bottom, back, and side interior of the housing 18 to reduce heat losses from the warming chamber 20. The insulating members 32 preferably allow the housing 18 to retain heat therein so as to reduce the amount of time needed to transform the thermoplastic material 14 into a pliable state. Moreover, the insulating members 32 preferably allow the housing 18 to attenuate noise generated by the array 22 of circulation elements 24 and the movement of air within the warming chamber 20. At 5,000 RPM (revolutions per minute), each circulation element 24 can generate sound levels up to 44 decibels (dB). In the array 22, the circulations elements 24 and the air flow resulting from their operations may generate noise level in excess of 50 dB. Such sound levels present an inconvenience and a potential hearing hazard to nearby operators in a limited work area. The insulating members 32 are designed into the housing 18 to attenuate the noise preferably to a level comparable to other instruments and devices in the therapy or orthopedic settings. Sound dampening components, such as plastic washers, may be installed between panels forming the housing 18 to reduce mechanical vibrations from the array 22 of circulation elements 24. In the preferred embodiment of the invention, the insulating members 32 may be a silica aerogel-based insulation blanket. The blanket may be hydrophobic and has a thermal conductivity preferably between 20 and 25 mW/m-K over the operating temperature of the device 10. In the preferred embodiment, the blanket is preferably at least 0.20 inch thick, even more preferably between 0.20 and 1.0 inch thick. Certain interior portions such as the top, front, rear, and side walls may employ thicker blanket thickness, such as at least about 0.40 inch.

Figure 4:
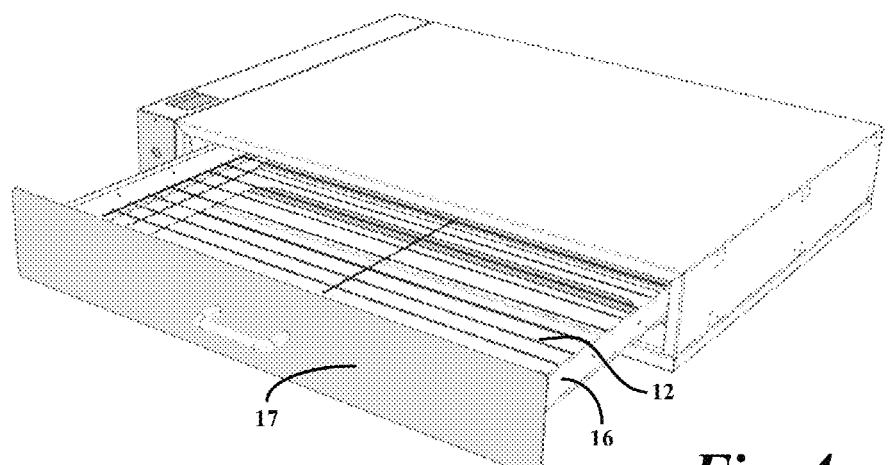
FIG. 4 is a perspective view of the device of FIG. 1 in an opened position.

With reference now to FIG. 4, the support member 12 may be in the form of a heat conductive panel or a grill and preferably extends substantially along the entire length of the warming chamber 20. The material from which the support member 12 is made must also allow the support member 12 to maintain its structural integrity when it is heated to a temperature range corresponding to the temperature range necessary for transforming a sheet 34 of thermoplastic material 14 into a more pliable state. A material such as aluminum, copper, or stainless steel is presently preferred. The support member 12 may be coated with an optional non-stick coating to prevent bonding of the thermoplastic material 14 to the support member 12. In some instances, the thermoplastic material 14, when warmed to a temperature sufficient to make it pliable, may stick to the support member 12. Thus, by having a non-stick coating on the support member 12, the release characteristic between the thermoplastic material 14 and the support member 12 may improve. A non-stick coating similar to a Teflon coated fiberglass cloth, which can withstand an application temperature of up to 500° F., is currently preferred. In one embodiment of the invention, a non-stick layer 41 (see FIG. 3) preferably has a thickness ranging from approximately 0.014 inch to approximately 0.110 inch, and is provided about the entire periphery of the support member 12. It should be appreciated that the non-stick layer 41 provided only on the one side of the support member 12 in contact with the sheet 34 of thermoplastic material 14 is sufficient.

Figure 7:
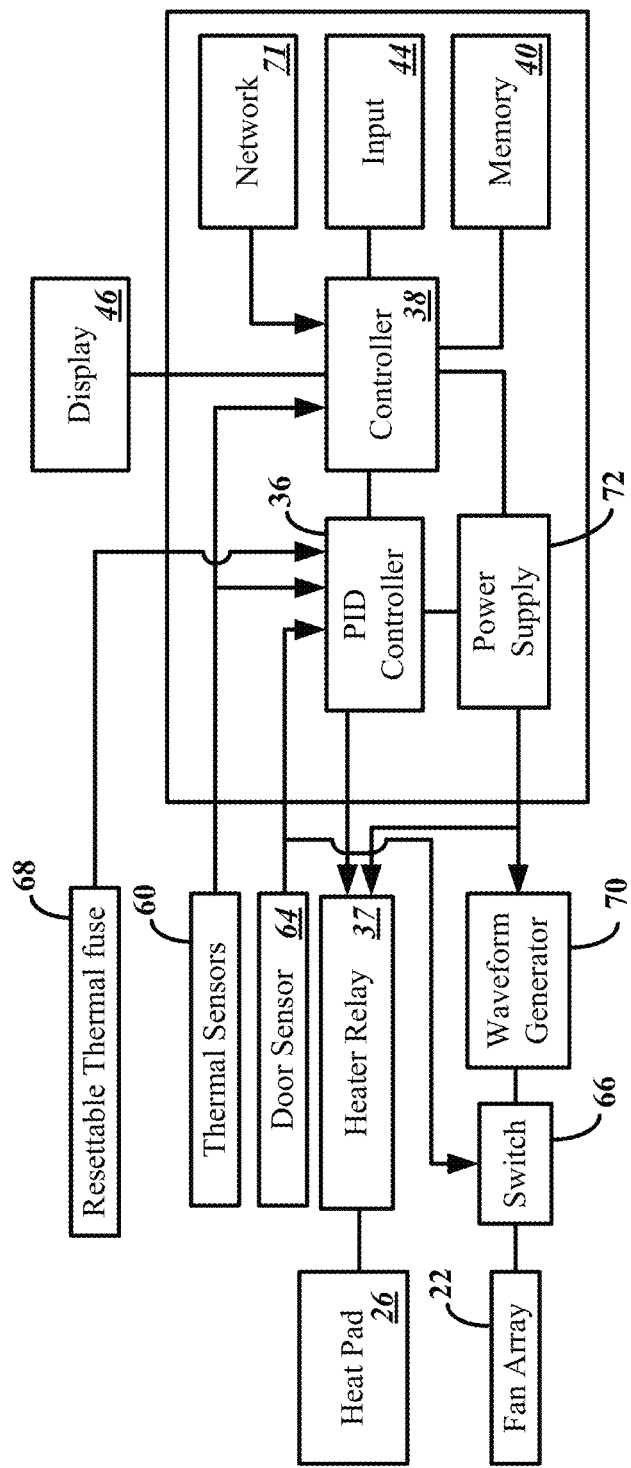
FIG. 7 is a schematic diagram of an apparatus for warming thermoplastic materials for purposes of patient fixation.

Referring to FIG. 7, the device 10 further includes a temperature regulator 36 (referred to in the figure as a "PID controller 36"). The temperature regulator 36 controls the temperature of the warming chamber 20 at a threshold temperature sufficient to allow the thermoplastic material 14 to transform in a pliable state by regulating the operation of the heating element 26. This threshold temperature is preferably the maximum rated temperature for the thermoplastic material 14. In the presently preferred embodiment of the invention, the set threshold temperature is within a range of from about 140° F. to about 180° F., depending on the thermoplastic material 14 being used. For example, if the thermoplastic material 14 is polycaprolactone, a set temperature of about 160° F.±0.5° F. is needed. The temperature regulator 36 eliminates the need to constantly check the status of the thermoplastic material 14 while it is in the device 10. In particular, the regulator 36 ensures that once the heating element 26 has reached the set threshold temperature, the heating element 26 does not generate heat beyond, or cool down below the required temperature. Additionally, if the device 10 is idle for a specified period of time, the regulator 36 may enter an idle state, setting the temperature within the warming chamber 20 to a drop-down temperature. The drop-down temperature is the temperature value for the device 10 in which the thermoplastic material 14 may be warmed for a long period time without affecting its long term material characteristic. To this end, the temperature is such that the thermoplastic material 14 may be kept near pliable, but is not sufficient to cause heat denaturation or burning. In this manner, the thermoplastic material 14 may remain indefinitely within the device 10, or until the thermoplastic material 14 is intended to be used. The time period to enter the idle state is preferably between about 0.5 hour and 3 hours, even more preferably at about 2 hours, either after the thermoplastic material 14 is in a pliable state or after the temperature within the warming chamber 20 has reached the set temperature. The regulator 36 preferably operates a heater relay 37 that controls power to the heating element 26 (referred to in the figure as "heat pad 26"). The presently preferred temperature regulator 36 and relay 37 are integrated in a single device having at least one temperature sensor input from the thermal sensor 60, and a dual control output. Other types of temperature sensors, such as, but not limited to, infrared sensors, resistance temperature detectors (RTD), thermistors, may be employed. In an embodiment, the thermal sensor 60 is preferably a thin-film platinum-based resistance thermometer.

The device 10 may include a controller 38, in accordance with an embodiment of the invention, to allow for the user to select a specific thermoplastic material 14 to be placed in the device 10. The controller 38 interfaces with a memory 40 having a library of thermoplastic materials 14. For each thermoplastic material 14 in the library, the memory 40 stores operational information for the material, including at least a maximum rated temperature value. The controller 38 is operatively linked to the temperature regulator 36 to provide the maximum rated temperature value as the set control temperature for the regulator 36. To this end, the user can configure the device 10 for different thermoplastic materials 14 and the optimal temperature controls profile for it with a single input selection. In an embodiment, the user selects the thermoplastic material 14 from a graphical user interface having an input 44 and a display 46. The input 44 preferably include discrete buttons, a keyboard, or a touchscreen display. In addition to the maximum rated temperature value, the memory 40 preferably stores other information associated with each thermoplastic material 14. Such information may include an image of the thermoplastic material 14, the manufacturer's name, the product name, the size of the sheet 34, the intended fixation location on the patient, as well as other control temperatures for heating the thermoplastic material 14. The display 46 preferably measures approximately 6 inches wide and 4 inches high. In an embodiment, the temperature regulator 36, the controller 38, and memory 40 are preferably implemented within a single microprocessor or microcontroller.

Figure 8:
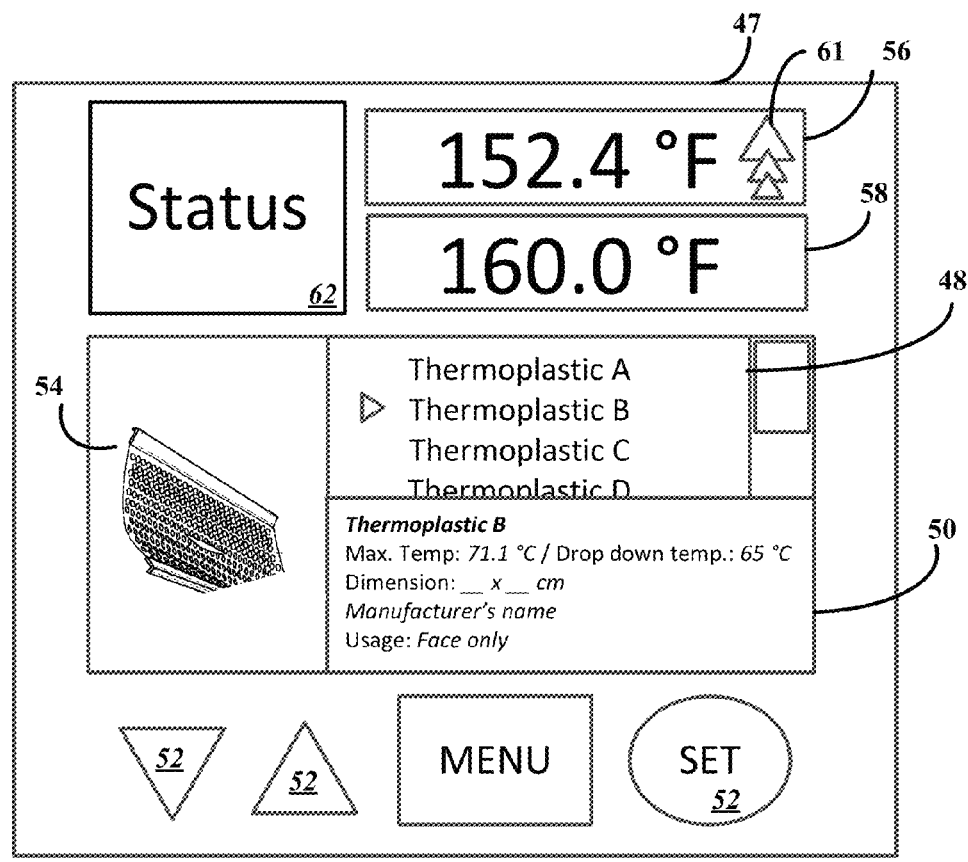
FIG. 8 is a front view of a control panel disposed on a display portion that connects to the device of FIG. 1.

Referring now to FIG. 8, the graphical user interface 47 displays a list 48 of thermoplastic materials 14 stored within the memory 40. The interface 47 preferably displays, in a selection panel 50, information associated with the selected thermoplastic material 14. For example, the selection panel 50 may display an identifier of the selected thermoplastic material 14, the maximum rated temperature, the drop down temperature, the dimensions of the thermoplastic material 14, the manufacturer's name, and the intended usage. Of course, other information may be stored including notes that that the user has associated with a thermoplastic material 14. The interface 47 preferably displays button objects 52 that receive inputs from the user for moving a selection cursor through the list 48 of thermoplastic materials 14. The interface 47 preferably displays an image 54 of the thermoplastic material 14 to aid the operator in verifying that the correct selection has been made. The graphical user interface 47 is preferably a color touchscreen with capacitive-based sensing mechanism. Of course, other touchscreen sensing mechanisms may be employed. In addition, the interface 47 may display the current temperature value 56 within the warming chamber 20 and the target set temperature value 58. The interface 47 may display an indicator object 61 associated with its operations. For example, the indicator object 61 may appear as a group of icons indicating the temperature is increasing and, optionally, the degree of the gain. Different icons may be employed to display the temperature being maintained or being decreased. The device 10 may further display the status 62 of the device 10. Such status may include "ready", "heating", "standby", and "off." The status 62 may be a part of the graphical user interface 47 or it may be an LED indicator co-located at the front of the device 10.

Referring to FIG. 7, the controller 38 or the regulator 36 may receive readings from thermal sensors 60 disposed in the warming chamber 20. More particularly, the thermal sensor 60 is preferably placed between the direct flow axes of two circulation elements 24. In an embodiment, the thermal sensor 60 is placed above the support member 12 in a manner to be above the thermoplastic material 14, such as to the top of the housing 18 (see FIGS. 2 and 3). In this manner, the thermal sensor 60 senses less variability in the temperature readings for the regulator 36. It was found that with a thermal sensor 60 configured in such manner changes in the temperature of the warming chamber 20 are sensed more quickly and, thus, allow the regulator 36 to control the temperature more precisely. Of course, additional thermal sensors may be employed within the warming chamber 20 to monitor, for example, the support member 12 and the heating element 26. The thermal sensor 60 is preferably a platinum-based resistance thermometer, such as, but not limited to, PT100 sensors. The device 10 is designed to quickly ramp from a dwell temperature 63 to the desired temperature, preferably between about 160° F. and about 180° F., with a small over-shoot temperature in the temperature and a small variability in the steady state temperature once there. In an embodiment, the dwell temperature 63 may be set in the regulator 36 as the drop-down temperature. FIG. 9 shows the over-shoot temperature 65 being less than 2° F. and variability of the steady state temperature 67 being less than 1° F. The ramp up time coincides with the time sufficient to transform the thermoplastic material 14 from a relatively rigid state to a more pliable state and is preferably less than five minutes.

The device 10 is designed with mechanisms to reduce the time for it to reach the desired steady state temperature to transform the thermoplastic material 14 from the rigid state to the pliable state and to provide safety functions. For example, the controller 38 or regulator 36 preferably discontinues power to the heating element 26 without intervention from the user upon detecting at least one faulty condition, such as an out of range reading from the thermal sensor 60. To that end, the readings may be subjected to minimal fluctuation. In addition, a sensor 64, preferably a momentary switch, is disposed on the housing 18 to determine the position of the drawer. The sensor 64 drives a switch, such as a relay 66, that powers the array 22 of circulation elements 24 (referred in the figure as "fan array 22"). This mechanism turns off the circulation of the heated air by discontinuing operations of the circulation elements 24 when the door of the housing 18 is opened. The preservation of heat in the warming chamber 20 reduces the energy, as well as the time, to ramp the temperature therein to the desired warming temperature. The door signal from the sensor 64, when the door is opened, may additionally trigger the shut-off of the heating element 26. To further reduce the warming time and limit energy consumption, the controller 38 or regulator 36 preferably includes a standby function, which maintains the temperature of the warming chamber 20 at the dwell temperature, preferably between about 120 and 125° F. The dwell temperature may be the drop-down temperature. The device 10 includes an electronic resettable thermal fuse 68 to disable the heating element 26 when over a maximum temperature value, preferably at about 180° F. (for example, see fuse 74 in FIG. 11(b)). Additionally, the controller 38 and/or regulator 36 may include a maximum settable temperature preferably between about 170° F. and about 180° F.

The device 10 may include a waveform generator 70 to condition the output of the power supply 72 to the array 22 of circulation elements 24. The waveform generator 70 may be a three-phase or six-phase DC-to-DC convertor to reduce noise generated by the circulation elements 24 and to improve the controls of the circulated output of the array 22. The power supply 72 may include a double fuse to protect the line input. The heating elements 26 may include a zero-voltage turn-on relay to eliminate power surges at the initiation of the heating cycle and to reduce electromagnetic interference (EMI). The device 10 preferably includes a network port for operatively communicating to a network. To this end, the device 10 may receive updated and additional library information for the thermoplastic materials 14 stored in the memory 40.

The device 10 advantageously warms a sheet of thermoplastic material 14 in a dry environment. In particular, as the heat is applied to the sheet 34 of thermoplastic material 14 through a dry circulated convective path, the sheet 34 may be transformed from a relatively rigid state to a more pliable state, more quickly and with less variability. Additionally, the transformation is in a safe, dry and clean environment, such that the chances of accidentally contaminating an otherwise clean work area are minimized. The sheet 34 of thermoplastic material 14, while pliable, may subsequently be molded into a cast 15, as shown in FIGS. 7-8, having a shape for complementarily receiving a part of a patient which requires immobilization.

To warm the sheet 34 of thermoplastic material 14, such as polycaprolactone, the sheet 34 may be placed on the supporting member 12, preferably having a non-stick surface 41, as illustrated in FIG. 3. The support member 12, with the thermoplastic material 14 thereon, may thereafter be moved to within the housing 18. Next, the temperature regulator 36 may be set to a threshold temperature sufficient to transform the sheet 34 of thermoplastic material 14 from a relatively rigid state to a more pliable state. Alternatively, the device 10 of the present invention may be preheated to the desired temperature prior to placing the sheet 34 of thermoplastic material 14 within the housing 18. It should be appreciated that heat transference from the heating element 26 to the thermoplastic material 14 is substantially by active convection. Heat from the heating element 26 is caused to be circulated by the array 22 of circulation elements 24. In the preferred embodiment, the array 22 pushes the heated air centrally into the central region 28 of the warming chamber 20 while drawing the heated air from the periphery region 30. The circulating air accelerates the phase transformation on a top and bottom surface of the thermoplastic material 14. Once the sheet 34 of thermoplastic material 14 has reached the desirable pliable state, the sheet 34 may be pulled from within the housing 18, and removed from the support member 12. The sheet 34 of thermoplastic material 14, while still pliable, may be molded into a cast 15 having an appropriate shape for immobilizing a particular body part on the patient. The sheet 34 of thermoplastic material 14 can subsequently be cast about that particular body part and allowed to harden.

The device 10 provides means for storing, in memory, information of a list of thermoplastic materials 14. The list is displayed on display 46 to receive input from a user selecting one of the thermoplastic materials 14. The device 10 determines a set temperature associated with the selected thermoplastic material 14 from the stored information. The controller 38 displays an image 54 of the thermoplastic material 14 and other information associated with the use of the thermoplastic material 14. To this end, the user can verify that the correct thermoplastic material 14 has been placed in the device 10. The thermal regulator 36 engages the relay 37 to the heater elements 26 to heat the warming chamber 20 to the set temperature, preferably with an over-shoot temperature of less than 2° F. The regulator 36 maintains the warming chamber 20 at the set temperature, preferably with variations in the temperature less than 1° F.

The embodiments of the invention described above are intended to be merely exemplary; numerous variations and modifications will be apparent to those skilled in the art. All such variations and modifications are intended to be within the scope of the present invention as defined in any appended claims. For example, the circulation elements may push air in at the periphery and pull from the center. Alternative arrangements may mix the inflows and outflows with additional fans. Additionally, wave guides may be added to help shape air flow vectors within the warming chamber.

What is claimed is:

1. An apparatus for warming a thermoplastic material for use on a patient, comprising:
    a housing defining a warming chamber having a central region and a periphery region;
    a support member disposed in the warming chamber, the support member having a surface for supporting a thermoplastic material;
    a heating element for distributing heat over a planar surface area coincident with the support member;
    an array of fans disposed along one wall of the warming chamber, wherein at least one of the fans is oriented for drawing air through the fans in a direction out from the warming chamber and wherein at least one other of the fans in the array is oriented for pushing air through the at least one other of the fans in the array in a direction into the warming chamber;
    a thermal sensor disposed in the central region of the warming chamber above the support member; and
    a thermal regulator responsive to the thermal sensor for maintaining the warming chamber at a set temperature; and
    wherein the support member is vertically spaced from the heating element to permit air to flow to and from the array of fans both above and below the support member to uniformly heat both sides of the thermoplastic material.

2. The apparatus of claim 1, wherein the housing includes a panel connected to the support member to form a drawer, the drawer being alternatively moveable between a closed position and an open position with respect to the warming chamber.

3. The apparatus of claim 2, wherein the heating element and the array of fans operate only when the drawer is in the closed position.

4. The apparatus of claim 1 wherein the regulation by the thermal regulator results in a variation of temperature within the warming chamber of less than one degree Fahrenheit from the set temperature.

5. The apparatus of claim 4, wherein the thermal regulator ramps the warming chamber to the set temperature in a manner that the temperature within the warming chamber does not exceed two degrees Fahrenheit of the set temperature.

6. The apparatus of claim 1 wherein the array of fans are horizontally-aligned.

7. The apparatus of claim 6 wherein the at least one other of the fans in the array oriented for pushing air through the at least one other of the fans in the array in a direction into the warming chamber is located nearer toward the center of the array than the at least one of the fans oriented for drawing air through the fans in a direction out from the warming chamber.

8. The apparatus of claim 1 further comprising a controller having a memory storing therein information for a plurality of thermoplastic materials, the controller having a user-input for selecting at least one of the plurality of thermoplastic materials, the controller being configured to set the set temperature of the thermal regulator based on the selected user-input.

9. The apparatus of claim 8, wherein the information further includes, for each of the plurality of thermoplastic materials stored in memory, an image of the thermoplastic material.

10. The apparatus of claim 1 wherein the thermal sensor is positioned between a direct flow axis of the at least one fan of the array of fans and a direct flow axis of a second fan of the array of fans pushing air in a direction into the warming chamber.

11. The apparatus of claim 1, wherein each fan generates a flow of between about 40 and 60 cubic feet per minute.

12. The apparatus of claim 1, wherein the heating element is configured as a planar surface spanning the central and periphery regions of the warming chamber.

13. The apparatus of claim 1, wherein the heating element is disposed below the support member, and wherein the array of fans is disposed above and below the support member.

14. The apparatus of claim 1 further comprising:
    a voltage waveform circuit for energizing the array of fans.

15. The apparatus of claim 1 being configured and sized for use on a countertop.

16. The apparatus of claim 1 wherein the surface of the support member comprises a non-stick surface.

* * * * *